United States Patent [19]

Shull

[11] 4,404,286

[45] Sep. 13, 1983

[54] BILIRUBIN ASSAY

[75] Inventor: Bruce C. Shull, Indianapolis, Ind.

[73] Assignee: The Dow Chemical Company, Midland, Mich.

[21] Appl. No.: 351,073

[22] Filed: Feb. 22, 1982

[51] Int. Cl.³ .................. G01N 33/72; G01N 33/92
[52] U.S. Cl. ........................................ 436/97; 422/61; 436/71; 436/175; 436/903
[58] Field of Search .............. 252/408; 23/905, 929, 23/909, 230 B; 422/61; 436/97, 903, 175, 71

[56] References Cited

U.S. PATENT DOCUMENTS

| | | | |
|---|---|---|---|
| 2,737,501 | 3/1956 | Sherman | 252/408 |
| 3,853,473 | 12/1974 | Morin et al. | 23/230 B |
| 4,030,885 | 6/1977 | Das | 252/408 X |
| 4,078,892 | 3/1978 | Steinbrink, Jr. | 422/61 X |
| 4,282,001 | 8/1981 | Klose et al. | 23/909 X |
| 4,311,483 | 1/1982 | Perry | 23/905 X |

*Primary Examiner*—Arnold Turk
*Attorney, Agent, or Firm*—Stephen L. Nesbitt; Raymond A. McDonald; Gary D. Street

[57] ABSTRACT

An improved reagent and method for assay of total bilirubin in biological fluids utilizes diazo sulfanilic acid to convert bilirubin to azobilirubin which is then quantitatively measured. The improved reagent and method include the solvent accelerator tetramethylene sulfone. The use of tetramethylene sulfone as also allows the use of nonionic surfactants, obviating the need for serum blank correction in highly lipemic serum. Furthermore, the use of tetramethylene sulfone and nonionic surfactants renders the reagent mixture less viscous facilitating automated analysis.

12 Claims, No Drawings

BILIRUBIN ASSAY

The formation of bilirubin occurs mainly from the catabolism of hemoglobin in the reticuloendothelial system. Bilirubin is then released into the bloodstream where it binds firmly to albumin and where it is referred to as "unconjugated" bilirubin. After transport and uptake by the liver, bilirubin is converted to polar conjugates, principally bilirubin diglucuronide, and is referred to as "conjugated" bilirubin. These polar conjugates are then excreted into the biliary tract and largely eliminated via the intestines.

Elevation of total serum bilirubin may occur due to hemolytic processes, liver disease, or disorders of the biliary tract. Elevation of total bilirubin which results in jaundice, may be due to excessive concentrations of either unconjugated or conjugated bilirubin.

In hemolytic disorders, such as hemolytic disease of the newborn, total bilirubin is increased by excessive formation. The rise in total bilirubin is due to increased levels of unconjugated bilirubin. Monitoring of total bilirubin is especially important in newborns because excessive levels of unconjugated bilirubin may cause brain damage, a syndrome known as kernicterus.

Diseases of the liver, such as hepatitis and cirrhosis, result in elevated total bilirubin due to disturbances of bilirubin metabolism. Both unconjugated and conjugated bilirubin levels may increase. Elevations of conjugated bilirubin are most common because excretion of conjugated bilirubin appears to be the rate limiting step in the hepatic clearance of bilirubin.

The elimination of conjugated bilirubin through the biliary tract is impaired in obstructive disorders (e.g., gallstones) and inflammatory disorders of the gallbladder. This blockage results in leakage of conjugated bilirubin into the bloodstream with resulting evaluated levels.

Accordingly, assay for bilirubin is a useful and widely used tool in the diagnosis and treatment of a variety of hemolytic disorders, liver diseases and biliary tract disorders.

The assay of total bilirubin is commonly performed utilizing diazo sulfanilic acid to form a colored azobilirubin product. This reaction is, however, quite slow in the absence of an accelerator. In the widely used Malloy-Evelyn assay (*J. Biol. Chem.*, 119, 481/1937), methanol is used as the diazo reaction accelerator, while caffeine is used in the Jendrassik-Grof assay (*Biochem. Z.*, 297, 81/1938). Walters and Gerarde (*Microchem. J.*, 15, 231/1970) developed a method in which dimethylsulfoxide (DMSO) is used as the accelerator at low pH.

Certain presently used reaction solvents and accelerators however, are unacceptable for a variety of reasons. Methanol causes precipatation of serum proteins. Dimethylsulfoxide as well as ethylene glycol, which is used as a solvent in some methods, are quite viscous and are not readily adaptable for use in flow system analysis.

The applicant has discovered that tetramethylene sulfone (TMS), when used as a solvent in total bilirubin assay by the diazosulfanilic acid procedure not only acts as a reaction accelerator but avoids the precipitation of serum proteins as occurs with methanol and is considerably less viscous than ethylene glycol or DMSO, facilitating automated flow system analysis. Moreover, the use of TMS allows the use of nonionic surfactants, which improves the flow properties of the reagent in flow cell instruments and eliminates blank interference arising from sample lipemia. Although DMSO based reagents allow the use of surfactants, unlike the TMS based reagent system of the present invention, the use of surfactants in DMSO based reagents results in lowered color yield and nonlinear assay results. The method of the instant invention yields linear results up to about 20 mg/dL of bilirubin in the presence or absence of nonionic surfactants.

The improved assay involves the addition of sodium nitrite to the reagent, containing sulfanilic acid, a mineral acid and TMS, to form diazo sulfanilic acid. On addition of a bilirubin containing biological fluid, the reaction of bilirubin with diazo sulfanilic acid in the presence of TMS and optional nonionic surfactants, results in the rapid formation of a stable azobilirubin product which can be photometrically quantitated at, for example, 565 nanometers (nm).

Bilirubin containing biological fluids which can be assayed by the procedure of the present invention include bilirubin containing blood serum or plasma, cerebrospinal fluid, amniotic fluid and lymphatic fluid. The biological fluid to be assayed can be obtained from any mammal such as dogs, cats, rats, mice, horses, cattle or humans. Of particular interest as a bilirubin containing biological fluid for assay is human blood serum. The use of fresh serum or plasma, which has been protected from light, is advisable in order to prevent decreased values due to photo-oxidation. Bilirubin in serum is stable for approximately 2 days at room temperature, up to 7 days when refrigerated or for at least 3 months frozen if kept in the dark.

In order to assure maximum shelf life, the various components, utilized in the assay procedure of the present invention, are maintained as three separate reagents and are mixed shortly before use. In this manner, the separate solutions are stable for up to 2 years when stored at room temperature (below 86° F.) and out of direct sunlight.

The first reagent, the bilirubin reagent, contains sulfanilic acid, a mineral acid and the tetramethylene sulfone (TMS) solvent accelerator.

Suitable mineral acids for use in the bilirubin reagent include phosphoric acid, sulfuric acid or preferably hydrochloric acid. The concentration of hydrochloric acid in the bilirubin reagent can be from about 0.01 to 0.20 mole/liter or an equivalent amount of any other mineral acid. The applicant has found that a hydrochloric acid concentration of less than 0.09 mole/liter results in diminished sensitivity and accordingly, a hydrochloric acid concentration of greater than 0.09 mole/liter is preferred. In a preferred embodiment, the bilirubin reagent is 0.18 N hydrochloric acid.

Sufficient sulfanilic acid must be utilized so that the amount of diazo sulfanilic acid formed therefrom, be adequate to cause complete conversion of the bilirubin to be assayed, to azobilirubin. Accordingly, it is recommended that the bilirubin reagent have a sulfanilic acid concentration of from about 10 to 30 mmole/liter. In a preferred embodiment of the present assay system, the bilirubin reagent contains 0.5% (w/v) sulfanilic acid.

The concentration of TMS in the bilirubin reagent can be from about 20 to 80% (v/v). Because a TMS concentration below about 40% results in diminished sensitivity, it is preferred that the TMS concentration in the bilirubin reagent be greater than 40%. In a preferred embodiment, the bilirubin reagent is 50% (v/v) TMS.

The second reagent, the surfactant reagent, contains one or more nonionic surfactants in a solvent. Suitable nonionic surfactants are, for example, an ethoxylated alkyl phenol of the general formula $C_9H_{19}C_6H_4(OCH_2CH_2)_nOH$ wherein the average value of n can be from about 2 to 10, preferably 4; a polyethylene glycol ether of oleyl alcohol of the general formula $CH_3(CH_2)_7CH=CH(CH_2)_7CH_2-(OCH_2CH_2)_nOH$ wherein the average value of n can be from about 5 to 50; a polyethylene glycol ether of lauryl alcohol of the general formula $CH_3(CH_2)_{10}CH_2(OCH_2CH_2)_nOH$, wherein the average value of n can be from 1 to 40, preferably 23; an ethoxylated alkyl phenol of the general formula $C_8H_{17}C_6H_4(OCH_2CH_2)_nOH$, wherein the average value of n can be from 1 to 40, preferably about 9; a mixture of laurate esters of sorbitol and sorbitol anhydrides of the general formula

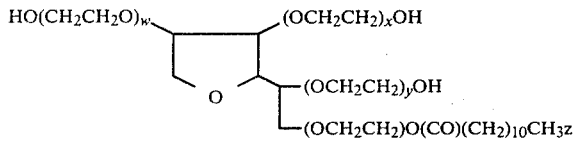

wherein the sum of $w+x+y+z$ is an integer of from 10 to 30, preferably 20. The preferred nonionic surfactant for use in the surfactant reagent in the improved bilirubin assay, is an ethoxylated alkyl phenol of the formula $C_9H_{19}C_6H_4(OCH_2CH_2)_nOH$ wherein n has an average value of 4 which is sold by the Union Carbide Company under the name Tergitol NP14, by Stepan Chemical Industries under the name Makon 4 and by Rohm and Haas under the name Triton N42.

The nonionic surfactant is diluted with solvent primarily to reduce the viscosity of the surfactant reagent. This reduced viscosity renders measurement and transfer of the surfactant reagent by pipet less difficult. A suitable solvent for use in the surfactant reagent is any organic solvent in which the surfactant is soluable, for example, methanol, ethanol, butanol or acetone. Methanol is the preferred solvent. The amount of solvent employed in the surfactant reagent is, accordingly, not critical. For practical reasons, the amount of solvent may vary from about 20% to 80% (v/v), preferably from about 40% to 60% (v/v). In a preferred embodiment, the surfactant reagent will comprise 60% (v/v) Triton N42 and 40% (v/v) methanol.

The surfactant reagent, which is optional, has a potent clarifying action on lipemic sera. Triglyceride levels up to 1000 mg/dL (grossly lipemic) do not require a serum blank correction. With some rare sera, slight elevation of results may occur due to incomplete clarification. Reduction of sample volume or use of a serum blank may then be used.

The third reagent, the nitrite reagent, contains a source of nitrite ion such as an alkali or alkaline earth metal nitrite, preferably sodium nitrite. The nitrite reagent of choice for use in the assay of the present invention consists of a aqueous solution of 0.5% w/v sodium nitrite.

Although it is recommended that the three reagents be combined shortly before use in the bilirubin assay procedure, the combined reagents are stable for about one day and may, for convenience, be prepared in advance.

Upon mixing the diazo sulfanilic acid, formed by mixing the 3 reagent solutions described above, and the bilirubin containing biological fluid, azobilirubin is formed after a short reaction period. This incubation period, preferably, does not exceed one hour, more preferably is from 5 to 10 minutes and most preferably is about 5 minutes. In any event, the color formation due to azobilirubin must be complete and the color measured before significant color degradation occurs. The final color is stable for at least one hour at room temperature, particularly, if direct sunlight is avoided. The color is quantitatively measured, typically, photometrically at 565 nm and compared to the color produced by reaction of the diazo sulfanilic acid, formed by mixing the 3 reagent solutions described above, and a known standard solution of bilirubin. Concentration is calculated from the following equation.

$$\frac{\text{mg total bilirubin}}{dL \text{ of sample}} = \frac{A(\text{sample})}{A(\text{standard})} \times \text{Standard}$$

wherein
A(sample) = Absorbance of unknown sample.
A(standard) = Absorbance of standard sample.
Standard = Concentration of standard in mg/dL.

The regular use of serum controls in both the normal and abnormal range is recommended as part of a quality control program. It is good practice to run a normal and abnormal control with each batch of samples. The value of each control should fall within the acceptable limits. Control samples should be protected from light to prevent deterioration. It should be noted that by using controls, one evaluates the performance of the assay procedure and the instrument system.

The method of the instant invention yields linear results up to about 20 mg/dL bilirubin. If the total bilirubin in the sample exceeds this level, it is recommended that the assay be repeated with diluted serum.

When analyzing hemolyzed samples it is recommended that a serum blank be run to correct for the color of hemoglobin itself. When using a serum blank, hemoglobin levels up to 500 mg/dL do not interfere with bilirubin assay of samples containing up to 20 mg/dL unconjugated bilirubin.

The present invention also comprises a reagent kit for the determination of total bilirubin in a biological fluid which comprises a set of three separate reagent reservoirs each containing one of the three reagents described above; the bilirubin reagent, the surfactant reagent and the nitrite reagent.

EXAMPLE 1

Bilirubin Reagent

The bilirubin reagent consists of a solution containing 0.5% (w/v) sulfanilic acid and 50% (v/v) tetramethylene sulfone and which is 0.18 N in hydrochloric acid.

EXAMPLE 2

Surfactant Reagent

| Compound | % (v/v) |
|---|---|
| Triton N42 (Rohm and Haas) | 60 |
| Methanol | 40 |

EXAMPLE 3

Nitrite Reagent

A solution of 0.5% (w/v) aqueous sodium nitrite is prepared.

EXAMPLE 4

Total Bilirubin Assay of Human Blood Serum

A preferred embodiment of the improved total bilirubin assay of this invention, which is readily adapted for kit use, is carried out as follows:

(a) Transfer 2.8 ml of the bilirubin reagent of Example 1 to each of 4 empty vials appropriately marked sample, standard, control and blank.

(b) To each tube add 0.10 ml of the nitrite reagent of Example 3 and mix well.

(c) To each tube add 0.20 ml of the surfactant reagent of Example 2 and mix well.

(d) Add 0.20 ml of patients blood serum, bilirubin standard, control serum or water to the tube labeled sample, standard, control and blank, respectively.

(e) Incubate at room temperature for at least 5 minutes.

(f) Zero the spectrophotometer with the blank solution at 565 nm. Record the absorbance of the solutions labeled sample, standard and control.

I claim:

1. A method for the assay of total bilirubin which comprises incubating a mixture of bilirubin containing biological fluid, diazo sulfanilic acid, tetramethylene sulfone and a nonionic surfactant, and subsequently measuring the color produced.

2. A method of claim 1 wherein the bilirubin containing biological fluid is human blood serum.

3. A method of claim 1 wherein the nonionic surfactant is an ethoxylated alkyl phenol of the formula $C_9H_{19}C_6H_4(OCH_2CH_2)_nOH$ wherein n has an average value of 4.

4. In a reagent composition for the assay of total bilirubin in a bilirubin containing biological fluid which comprises diazo sulfanilic acid, the improvement wherein the reagent also comprises the solvent accelerator tetramethylene sulfone and a nonionic surfactant.

5. The improved composition of claim 4 wherein the nonionic surfactant is an ethoxylated alkyl phenol of the formula $C_9H_{19}C_6H_4(OCH_2CH_2)_nOH$ wherein n has an average value of 4.

6. A kit for total bilirubin assay which comprises
  (a) a bilirubin reagent comprising sulfanilic acid, a mineral acid and tetramethylene sulfone;
  (b) a surfactant reagent comprising a nonionic surfactant and a solvent; and
  (c) a nitrite reagent comprising a source of nitrite ion.

7. The kit of claim 6 wherein the mineral acid of the bilirubin reagent is hydrochloric acid.

8. The kit of claim 7 wherein the bilirubin reagent consists of a solution containing 0.5% w/v sulfanilic acid and 50% v/v tetramethylene sulfone and which is 0.18 N in hydrochloric acid.

9. The kit of claim 6 wherein the nonionic surfactant of the surfactant reagent is an ethoxylated alkyl phenol of the formula $C_9H_{19}C_6H_4(OCH_2CH_2)_nOH$ wherein n has an average value of 4.

10. The kit of claim 9 wherein the surfactant reagent is 60% v/v nonionic surfactant and is 40% methanol.

11. The kit of claim 6 wherein the source of nitrite ion in the nitrite reagent is sodium nitrite.

12. The kit of claim 11 wherein the nitrite reagent is a 0.5% aqueous solution of sodium nitrite.

* * * * *